US007481179B2

(12) United States Patent
Cantrell et al.

(10) Patent No.: US 7,481,179 B2
(45) Date of Patent: Jan. 27, 2009

(54) IN OVO ACTIVATION OF AN EGG IN THE SHELL

(76) Inventors: Tim Cantrell, 6622 Old Cleveland Rd., Clermont, GA (US) 30527; Andrew Wooten, 3520 W. Golden La., Chandler, AZ (US) 85226

( * ) Notice: Subject to any disclaimer, the term of this patent is extended or adjusted under 35 U.S.C. 154(b) by 0 days.

(21) Appl. No.: 11/824,229

(22) Filed: Jun. 29, 2007

(65) Prior Publication Data
US 2007/0261128 A1  Nov. 8, 2007

Related U.S. Application Data

(63) Continuation-in-part of application No. 09/784,575, filed on Feb. 15, 2001, now Pat. No. 7,237,505.

(60) Provisional application No. 60/182,969, filed on Feb. 16, 2000, provisional application No. 60/182,432, filed on Feb. 15, 2000.

(51) Int. Cl.
A01K 45/00 (2006.01)
A01K 67/027 (2006.01)
(52) U.S. Cl. .......................... 119/6.8; 800/19
(58) Field of Classification Search .................. 800/19; 119/6.8
See application file for complete search history.

(56) References Cited

U.S. PATENT DOCUMENTS

| 4,378,758 | A | 4/1983 | Coleman |
| 4,903,635 | A | 2/1990 | Hebrank |
| 5,136,979 | A | 8/1992 | Paul et al. |
| 5,158,038 | A | 10/1992 | Sheeks et al. |
| 5,176,101 | A | 1/1993 | Paul et al. |
| 5,339,766 | A | 8/1994 | Phelps et al. |
| 5,438,954 | A | 8/1995 | Phelps et al. |
| 5,529,792 | A | 6/1996 | Risau et al. |
| 5,699,751 | A | 12/1997 | Phelps et al. |
| 5,722,342 | A | 3/1998 | Line et al. |
| 5,900,929 | A | 5/1999 | Hebrank et al. |
| 7,237,505 | B2 * | 7/2007 | Cantrell et al. ............... 119/6.8 |

FOREIGN PATENT DOCUMENTS

| FR | 2623206 | 5/1989 |
| SU | 791357 | 12/1980 |
| WO | WO93/14629 | 8/1993 |
| WO | WO 93/15185 | 8/1993 |

OTHER PUBLICATIONS

Tanaka (Journal Reproduction and Fertility, 1994, vol. 100, p. 447-449).*
Johnston ("In vitro sperm binding, penetration, and fertilization of recently oviposited chicken eggs" Thesis, Graduate School of Clemson University, Dec. 1998).*
Goldberg (Ped. Res. 1992, vol. 32, p. 23-26).*
Alberts et al. "Egg Activation Is Mediated by Changes in Intracellular Ion Concentrations[16,19]" *Molecular Biology of the Cell* 804-809, 1983.
Bakst and Howarth, Jr. "Hydrolysis of the Hen's Perivitelline Layer by Cock Sperm in vitro" *Biol Reprod.* 17:370-379, 1977.
Bakst et al. "Effects Of Isolation And Culture Of Turkey Primary Follicular Oocytes On Morphology And Germinal Vesicle Integrity" *Theriogenology* 50: 1121-1130, Nov. 1998.
Bakst, MR "Preservation Of Avian Cells" *Developments in Animal Veterinary Sciences* 22: 91-108, 1990.
Bakst, MR "Artificial Insemination Technology" in Manipulation of the Avian Genome *CRC Press* Boca Raton, FL 24-26, 1993.
Barnes et al. "Influence of Recipient Oocyte Cell Cycle Stage on DNA Synthesis, Nuclear Envelope Breakdown, Chromosome Constitution, and Development in Nuclear Transplant Bovine Embryos" *Molecular Reproduction and Development* 36:33-41, 1993.
Bosselman et al. "Germline Transmission of Exogenous Genes in the Chicken" *Science* 243: 533-535, 1989.
Bradley et al. "Formation of germline chimeras from embryo-derived teratocarcinoma cell lines" *Nature* (London), 309: 255-256, May 17, 1984.
Campbell et al. "Nuclear-Cytoplasmic Interactions during the First Cell Cycle of Nuclear Transfer Reconstructed Bovine Embryos: Implications for Deoxyribonucleic Acid Replication and Development" *Biology of Reproduction* 49, 933-942, 1993.
Cibelli et al. "Cloned Transgenic Calves Produced from Nonquiescent Fetal Fibroblasts" *Science* 280:1256-1258, May 22, 1998.
Collas and Robl "Factors Affecting the Efficiency of Nuclear Transplantation in the Rabbit Embryo" *Biol Reprod.* 43: 877-884, 1990.

(Continued)

*Primary Examiner*—Michael C. Wilson
(74) *Attorney, Agent, or Firm*—Ballard Spahr Andrews & Ingersoll, LLP

(57) ABSTRACT

The present invention relates to the field of avian reproduction. In particular, the present invention provides a method of activating an egg in a shell. The invention also provides a method of activating an egg in a shell, whereby a live chick is hatched.

8 Claims, No Drawings

OTHER PUBLICATIONS

Cuthbertson, KSR "Parthenogenetic Activation of Mouse Oocytes in Vitro with Ethanol and Benzyl Alcohol," *J Exp Zool.* 226: 311-314, 1983.

Etches and Gibbins "Strategies for the Production of Transgenic Chickens" *Methods Mol Biol.* 62:433-450, 1997.

Eusebi and Siracusa "An Electrophysiological Study of Parthenogenetic Activation in Mammalian Oocytes," *Developmental Biology*, 96:386-395, 1983.

Evans and Kaufman "Establishment in culture of pluripotential cells from mouse embryos" *Nature* (London), 292:154-156, 1981.

First et al. "Use Of In Vitro Matured Oocytes 24 Hr Of Age In Bovine Nuclear Transfer" *Theriogenology* 37(1):211, 1992.

Fissore and Robl "Intracellular $Ca^{2+}$ Response of Rabbit Oocytes to Electrical Stimulation" *Mol Reprod Dev.* 32: 9-16, 1992.

Fulka et al. "Effect of 6-Dimethylaminopurine on Germinal Vesicle Breakdown of Bovine Oocytes" *Mol Reprod Dev.* 29: 379-384, 1991.

Goldberg et al. "Cardiac teratogenicity of dichloroethylene in a chick model," *Pediatr Res*, 32(1):23-26, 1992.

Harada, K., et al. "The Chromosomes of Turkey Embryos During Early Stages of Parthenogenetic Development," *Genetics* 98: 335-345, Jun. 1981.

Johnston, SC "In vitro Sperm Binding, Penetration, and Fertilization of Recently Oviposited Chicken Eggs" *Poultry* Science, 77(Suppl. 1):142, 1998.

Kaufman, MH "Parthenogenesis in the Mouse" *Nature* 242: 475-476, 1973.

Kaufman, MH "Parthenogenesis: a system facilitating understanding of factors that influence early mammalian development" *Prog. in Anat.* 1: 1-34, 1981.

Kline and Kline "Repetitive Calcium Transients and the Role of Calcium in Exocytosis and Cell Cycle Activation in the Mouse Egg" *Dev Biol.* 149: 80-89, 1992.

Koyanagi and Nishiyama "Fate of Spermatozoa That Do Not Participate in Fertilization in the Domestic Fowl" *Cell Tissue Res* 214:89-95, 1981.

Kubiak, "Mouse Oocytes Gradually Develop the Capacity for Activation During the Metaphase II Arrest," *Dev Biol.* 136: 537-545, 1989.

Kuroki et al. "Binding of Spermatozoa to the Perivitelline Layer in the Presence of a Protease Inhibitor" *Poult Sci.* 5: 748-752, May 1997.

Landa and Hajkova "Diploidization of Bovine Oocytes Matured in Vitro and Parthenogenetically Activated by Electric Shock" *Folia Biologica* 36: 145-152, 1990.

Love et al. "Transgenic Birds by DNA microinjection" *Biotechnology* 12: 60-63, Jan. 1994.

Maeza and Buss "Sperm Concentration And Sperm Numbers As Related To Fertility In Chickens" *Poultry Science* 55(5): 2059, 1976.

Martin, G "Isolation of a pluripotent cell line from early mouse embryos cultured in medium conditioned by teratocarcinoma stem cells" *Proc Nat Acad Sci.* 78: 7634-7638, 1981.

Masui and Markert "Cytoplasmic Control of Nuclear Behavior during Meiotic Maturation of Frog Oocytes," *J Exp Zool.* 177: 129-146, 1971.

McGrath and Solter "Nuclear Transplantation in the Mouse Embryo by Microsurgery and Cell Fusion" *Science* 220: 1300-1302, 1983.

Nagai, T "Parthenogenetic Activation of Cattle Follicular Oocytes in Vitro with Ethanol" *Gamete Res.* 16:243-249, 1987.

Nakanishi and Iritani "Gene Transfer in the Chicken by Sperm-Mediated Methods" *Mol Reprod Dev.* 36(2):258-261, Oct. 1993.

Nakanishi et al. "Early Nuclear Events of in Vitro Fertilization in the Domestic Fowl (*Gallus domesticus*)" *Mol Reprod Dev.* 26(3): 217-221, Jul. 1990.

Nakanishi et al. "Fertilizing Competency of Multiple Ovulated Eggs in the Domestic Fowl (*Gallus domesticus*)" *Mol Reprod Dev.* 28(2):131-135, Feb. 1991.

Naito et al., "Development in culture of the chick embryo from fertilized ovum to hatching," *J Exp Zool.*, 254(3):322-326 1990.

Nurse, "Universal control mechanism regulating onset of M-phase" *Nature* 344: 503-508, 1990.

Okamura and Nishiyama "The Passage of Spermatozoa through the Vitelline Membrane in the Domestic Fowl, *Gallus gallus*" *Cell Tiss. Res.* 188: 497-508, 1978.

Olsen, MW "Maturation, Fertilization, And Early Cleavage In The Hen's Egg" *J Morph* 70: 513-533, 1942.

Olsen, MW, "Frequency of Parthenogenesis in Chicken Eggs," *Journal of Heredity* 57(1)23 (1966).

Ono, et al., "Mineral content of quail embryo cultured in mineral-rich and mineral-free conditions," *Poultry Science*, 63:159-166 (1984).

Onodera and Tsunoda "Parthenogenetic Activation of Mouse and Rabbit Eggs by Electric Stimulation In Vitro" *Gamete Research* 22: 277-283, 1989.

Ozil, JP "The parthenogenetic development of rabbit oocytes after repetitive pulsatile electrical stimulation" *Development* 109: 117-127, 1990.

Perry, " A complete culture system for the chick embryo," *Nature* 7;331(6151):70-72 1988.

Petitte et al. "Blastodermal Cell Transfer and Germline Chimeras" in *Manipulation of the Avian Genome CRC Press* Boca Raton, FL 84-85, 1993.

Petitte et al. "Production of somatic and germline chimeras in the chicken by transfer of early blastodermal cells" *Development* 108, 185-189, 1990.

Rickords and White "Electrofusion-Induced Intracellular $Ca^{2+}$ Flux and its Effects on Murine Oocyte Activation" *Mol Reprod Dev.* 31:152-159, 1992.

Robertson et al. "Characterization and application of an avian in vitro spermatozoa-egg interaction assay using the inner perivitelline layer from laid chicken eggs," *J Reprod Fertil.*, 110(2):205-211, 1997.

Salter et al. "Gene Insertion into the Chicken Germ Line by Retroviruses" *Poul. Sci.* 65: 1445-1458, 1986.

Sang et al. "Transfection of Chick Embryos Maintained Under in Vitro Conditions" in Manipulation of the Avian Genome *CRC Press* 121-133, 1993.

Sarvella, "Sporadic Occurrence of Parthenogenesis" Journal Of Heredity, 61(5):215-219 (1970).

Sarvella, "Development of Parthenogenesis in Chickens" Poultry Science, 50(5):1626 (1971).

Sarvella, "Development of Parthenogenetic Membranes in Double-yolked and Injected Chicken Eggs," *J. Exp. Zool.*, 192:143-148 (1975).

Sherman et al. "Transposition of the *Drosophila* element *mariner* into the chicken germ line" *Nature Biotechnology* 16(11): 1050-1053, 1998.

Shuman RM "Production of transgenic birds" *Experientia* 47(9): 897-905, Sep. 15, 1991.

Siracusa et al. "Parthenogenetic activation of mouse oocytes induced by inhibitors of protein synthesis," *J. Embryol. Exp. Morph.* 43:157-166, 1978.

Sirard et al. "The Culture of Bovine Oocytes to Obtain Developmentally Competent Embryos" *Biol Reprod*.39:546-552, 1988.

Steinhardt, et al. "Is calcium ionophore a universal activator for unfertilized eggs?" *Nature* 252:41-43, 1974.

Stice and Keefer "Improved Developmental Rates for Bovine Nucleus Transfer Embryos Using Cold Shock Activated Oocytes" *Biol Reprod.* 462(Suppl 1): 166, 1992.

Stice and Robl "Activation of Mammalian Oocytes by a Factor Obtained from Rabbit Sperm" *Mol. Reprod. Dev.* 25:272-280, 1990.

Surani and Kaufmann "Influence of Extracellular $Ca^{2+}$ and $Mg^{2+}$ Ions on the Second Meiotic Division of Mouse Oocytes: Relevance to Obtaining Haploid and Diploid Parthenogenetic Embryos" *Dev Biol.* 59:86-90, 1977.

Susko-Parrish et al. "Effect Of Bovine Oocyte Aging In Vitro On Development" *Biol Reprod.* 44(Suppl 1): 17:156 (abstract), 1991.

Swann, K "A cytosolic sperm factor stimulates repetitive calcium increases and mimics fertilization in hamster eggs" *Development* 110: 1295-1302, 1990.

Tanaka et al. "Chick Production by in vitro fertilization of the fowl ovum" *J. Reprod. Fert.* 100:447-449, 1994.

Tarkowski et al. "Experimental Parthenogenesis in the Mouse" *Nature* 226: 162-165, 1970.

Tarkowski, AK "Induced Parthenogenesis in the Mouse" *The Developmental Biology of Reproduction* (C.L. Market, E.J. Papaconstantinon, eds.) 107-129, New York: Academic Press, 1975.

Thomas and Capecchi "Site Directed Mutagenesis by Gene Targeting in Mouse Embryo-Derived Stem Cells" *Cell* 51, 503-512, 1987.

Tombes et al. "Meiosis, Egg Activation and Nuclear Envelope Breakdown Are Differentially Reliant on $Ca^{2+}$, Whereas Germinal Vesicle Breakdown Is $Ca^{2+}$ Independent in the Mouse Oocyte" *J Cell Biol.* 117: 799-811, 1992.

Vick et al. "Transgenic birds from transformed primordial germ cells" *Proc R Soc Lon B Biol Sci.* 251(1332): 179-182, Mar. 22, 1993.

Wakayama et al. "Full-term development of mice from enucleated oocytes injected with cumulus cell nuclei" *Nature* 394: 369-374, Jul. 23, 1998.

Ware et al. "Age Dependence of Bovine Oocyte Activation" *Gamete Res.* 22: 265-275, 1989.

Watanabe et al. "Independent inactivation of MPF and cytostatic factor (Mos) upon fertilization of *Xenopus* eggs" *Nature* 352: 247-248, 1991.

Watanabe et al. "Specific proteolysis of the c-mos proto-oncogene product by calpain on fertilization of *Xenopus* eggs" *Nature* 342: 505-510, Nov. 30, 1989.

Wentworth et al. "Manipulation of Avian Primordial Germ Cells and Gonadal Differentiation" *Poultry Sci.* 68:999-1010, 1989.

Whitaker and Irvine "Inositol 1, 4, 5-trisphophate microinjection activates sea urchin eggs" *Nature* (London) 312:636-639, Dec. 13, 1984.

Yang et al. "Improved Activation By Combined Cycloheximide And Electric Pulse Treatment Of Bovine Follicular Oocytes Matured In Vitro For 23-24 Hours" Biol Reprod. 46 (Suppl 1): 117, 1992.

Yang et al. "Nuclear Transfer In Rabbits And Cattle By Electric Pulse-Induced Fusion Of Blastomeres To Enucleated Oocytes" *Theriogenology* 35(1): 298 (abstract), 1991.

Yang et al. "Potential of Hypertonic Medium Treatment for Embryo Micromanipulation: II. Assessment of Nuclear Transplantation Methodology, Isolation, Subzona Insertion, and Electrofusion of Blastomeres to Intact or Functionally Enucleated Oocytes in Rabbits," *Mol Repro and Dev* 27:118-129, 1990.

\* cited by examiner

IN OVO ACTIVATION OF AN EGG IN THE SHELL

CROSS-REFERENCE TO RELATED APPLICATIONS

This application is a continuation-in-part of Ser. No. 09/784,575, filed on Feb. 15, 2001, now U.S. Pat. No. 7,237,505, which claims priority to U.S. provisional application Ser. No. 60/182,432, filed Feb. 15, 2000, and U.S. provisional patent application Ser. No. 60/182,969, filed Feb. 16, 2000, which applications are hereby incorporated herein by reference in their entireties.

BACKGROUND OF THE INVENTION

1. Field of the Invention

The present invention relates to the field of avian egg activation. In particular, the present invention relates to methods of activating an egg in a shell. The invention also relates to a method of activating an egg in a shell, whereby a live chick is hatched.

2. Background Art

Traditional Breeding

Typically, breeding in the poultry industry is carried out by either one of two systems:

Floor Breeding Program. The first system is called "floor breeding" and it is utilized to produce the vast majority of all commercial hatching eggs. In this system males are simply added into the flocks of females at a typical ratio of between 10 and 15 percent. The floor breeding system, even with its inefficiencies, is currently the low-cost system for producing hatching eggs because it requires less labor than competing systems. Average hatch rates range from approximately 83% for broiler breeders to 92% for layer breeders. Even though this system has been the backbone of the poultry industry for many years, it has many limitations.

Size Versus Reproductive Capacity: Floor breeding is no longer practiced at all in turkeys due to the intense selection for increased muscle yield that has rendered commercial turkey breeds incapable of natural mating. The same trend is being seen in broilers. Selection for increased size in broilers has compromised fertility and mating ability and it is predicted that fertility will continue to decline as body weights increase. This presents a dilemma for poultry producers because decreases in fertility have a direct negative impact on their bottom line.

Inefficient Waste Removal: Natural mating must be performed on solid floors to avoid injury to the birds. This design requirement precludes the use of automated waste removal systems and necessitates manual cleaning between successive flocks of birds. This adds to labor and overhead costs while decreasing the productive use of facilities.

Egg Production & Quality: Since eggs remain in the houses with the flock until collection time; eggs are frequently contaminated with dirt and fecal material which can reduce hatch rates. In addition, typically between 3 and 5% of the eggs produced in floor houses are laid directly on the floor rather than in the provided laying boxes and must be discarded.

Inefficient Space and Equipment Utilization: Maintaining males and females together in a floor house requires the installation of two independent feed and watering systems because of different nutritional and production requirements for each sex. It also requires the installation of laying boxes and automated egg collection systems. All of this equipment occupies limited floor space in the house. For these reasons floor rearing is not an efficient use of housing space and equipment when compared to stacked cage systems.

Mortality & Fertility: Aggressive males tend to fight, leading to higher male mortality rates. Male mortality rates average 13% in floor houses versus 2% in cage houses. Male aggressiveness towards hens during mating gradually takes a toll in the form of increased female mortality, decreased fertility, and a decrease in the length of the egg production cycle. As the males in one flock get older, fertility starts to decline. The standard solution is to "spike" the flock with young males to improve fertility. However, this sets off another round of aggression with a short-term decrease in fertility and an increase in mortality. Disease is more common in floor houses because of the constant contact of the birds with bedding and waste material that harbor pathogenic organisms.

Decreased Feed Conversion: Controlling feed costs is critical to running a competitive poultry operation. Feed costs can account for up to 60% of the cost of raising a broiler chick, for instance. In one study, birds raised on the floor consumed 20% more food for the same amount of production when compared to those raised in cages. This difference is due to the increased level of social interactions as well as the generally higher level of physical activity seen in floor houses. Males consume more feed than females, making the floor breeding system inefficient with respect to feed consumption due to the large numbers of males that must be maintained.

Limited Flexibility in Breeding Strategies: Due to the fact that males and females are housed in one large group in the floor breeding house arrangement, the breeder is very restricted in their ability to perform advanced crosses and selections on the breeding stock. For this reason floor houses are primarily utilized as a tool for the multiplication of pre-selected genetic stocks to produce final commercial crosses.

Artificial Insemination Breeding Program: Another system utilized to generate hatching eggs is called artificial insemination (AI). AI is widely practiced by "primary breeders" at the top of the breeding pyramid but not generally used by commercial producers at the bottom of the pyramid. Primary breeders are companies that own and improve the elite pedigreed genetic lines that are crossed to produce the final commercial products—broilers, layers and turkeys. The quantities of birds increase exponentially as you move down the breeding pyramid from the pedigreed lines through the grandparent stock, parent stock, and finally to the actual commercial birds. While birds of elite genetic makeup at the top of the pyramid are very expensive, birds at the bottom are inexpensive. For these reasons, different operational models are utilized for reproduction at different level.

In the AI system, males and females are housed in the same houses but are caged separately. The female cages typically hold between two and five hens, while the male cages hold a single rooster. AI programs address many of the limitations of the floor breeding houses listed above. For example, since cage houses are utilized, waste removal can be performed automatically. Houses are generally much cleaner, leading to fewer disease problems. Egg production is improved because eggs roll out of the cages and is not laid on dirty floors. Equipment and housing space are utilized more efficiently. Mortality is minimized due to a decrease in social aggression and disease. Fertility levels are maintained more consistently because social and physical interaction are eliminated from the process of reproduction. Feed conversion is increased. And finally, the production system has increased flexibility for doing advanced crosses and selections. This capability is absolutely required by primary breeders in order to improve their genetic stocks and to stay competitive in the market-place. While most of the advantages listed above are also important for commercial-level multiplication breeders, they are offset by one crucial shortcoming, the high labor costs associated with AI programs.

AI programs replace the innate sexual drive of poultry with human labor. Workers must manually collect semen from males in cages and inseminate females in cages on a 7-day rotation. The level of sophistication required in these programs mandates a skilled workforce. For this reason, the AI program, though operationally superior, is economically impractical for commercial-level breeding programs. Even the use of dwarf hens, an innovation that allows similar egg production with about 30% less feed consumption, can not justify the increased labor costs of the AI program for commercial level multiplication breeders.

Reproductive Process

At the time of ovulation, the avian oocyte comprises a blastodisc, or germinal disc, which contains the female pronucleus, and a yellow yolk mass. The germinal disc and yolk mass are surrounded by the oocyte cell membrane, called the oolemma. Surrounding the oolemma is the perivitelline layer (PL), also referred to as the inner perivitelline layer (IPL). The space between the oolemma and the IPL is termed the perivitelline space, which is traversed by granulosa cells. Once the oocyte is released from its ovarian follicle, it is referred to as an ovum. The ovum moves into the oviduct where it is engulfed by the infindibulum, where fertilization occurs if sperm are present.

As the ovum passes into the posterior infindibulum, another layer, the outer perivitelline layer (OPL), surrounds the ovum. This membrane acts to prevent polyspermy, which is a lethal condition that occurs when multiple sperm bind to and penetrate the ovum at the region of the blastodisc. The egg is then surrounded with additional layers of chalaza and thick and thin layers of albumen. When the ovum moves into the isthmus, two shell membranes are deposited, upon which small crystals of calcium carbonate are deposited, thus beginning the formation of the shell.

The preceding events all occur within the first few hours following fertilization. The ovum next moves into the uterus, where over the next 18-20 hours, the calcium shell is completed. The egg then moves into the vagina for several minutes, and then is extruded from the vagina, or oviposited (i.e., "laid"). At this point, if the egg has been fertilized, the embryo contained therein will have 40,000 to 70,000 cells. (Johnston, "In Vitro Sperm Binding, Penetration, and Fertilization of Recently Oviposited Chicken Eggs," December 1988, Clemson University); Olsen, M. W., J. Morph. 70: 413-533 (1942); Etches et al., in Methods in Molecular Biology, vol. 62 *Recombinant Gene Expression Protocols*, Ed. R. Tuan, Humana Press, Inc. Totowa, N.J., pp. 433-450 (1997); Petitte et al., in *Manipulation of the Avian Genome*, Ed. Etches et al., CRC Press, Boca Raton, Fla., pp.81-101 (1993)).

Transgenesis

It has long been a goal of avian geneticists to supplement traditional selection procedures by inserting desirable genes directly into the avian germline. Substantial progress along these lines has been made in mammalian species where early embryos are accessible and where pronuclei can be visualized for the insertion of exogenous DNA. The production of transgenic mice, cattle, sheep, and goats has become a routine procedure in large commercial operations. In avian species, by contrast, the early embryo has not been easily accessed and the pronuclei are visually obscured, making manipulation of the avian genome in early embryos in ovo an almost insurmountable goal.

The development of genetically modified birds largely requires access to early stage, pluripotent embryonic cells. As the earliest stages of embryo development occur within the oviduct of the female, the introduction of heterologous DNA into the early embryo has only been possible by removing the embryo from the female, requiring that she be sacrificed. Furthermore, while culture of the early stage embryo to hatch has been accomplished, the method is extremely laborious, and results in a post-hatch survival rate of only about 10%. Sang et al., in *Manipulation of the Avian Genome*, Ed. Etches et al., CRC Press, Boca Raton, Fla., pp.121-133 (1993).

The present invention provides a ground-breaking improvement in avian biology by making it possible to activate an oviposited egg in its shell, and to hatch a live bird from the shell, herein called in ovo activation. Such methods provide an alternative to floor breeding and artificial insemination that can greatly increase the efficiency of poultry production. Such methods also provide access to early avian embryos such that transgenic avian species can be more readily developed.

SUMMARY OF THE INVENTION

The present invention relates to the field of avian reproduction. In particular, the present invention provides a method of activating an egg in a shell. The invention also provides a method of activating an egg in a shell, whereby a live chick is hatched.

Also provided by the present invention is a developmentally early stage oviposited avian egg.

DETAILED DESCRIPTION OF THE INVENTION

As used herein, "a," "an" or "the" may mean one or more. For example, "an" egg may mean one egg or more than one egg. Moreover, "the" egg may mean one egg or more than one egg.

As used herein, "activation" means the initiation of embryo development in an unfertilized oviposited avian egg or oocyte. Various forms of activation are set forth below. The process of activating an oviposited egg in a shell is referred to herein as "in ovo activation," (IOA).

The present invention provides a method of activating an avian egg in a shell, wherein the egg comprises a yolk enclosed by a membrane and an ovum, comprising activating the ovum. The present invention relates to the unexpected and surprising discovery that an unfertilized, oviposited avian egg can be activated in the shell and produce a live chick. As used herein, reference to an avian egg in a shell refers to an oviposited egg, that is, an egg with a calcium carbonate shell that has been extruded from the vagina of the bird. Extrusion of the egg is referred to as "oviposition." Accordingly, all references herein to an "egg in a shell" or to an "oviposited egg" should be understood to be equivalent in meaning.

An avian egg comprises a hard, calcified shell at the time the egg is oviposited. Within the shell is a yolk that contains nutrients for supporting growth and development of an embryo. As used herein, an "embryo" is a developing organism resulting from the joining of a female pronucleus and a male pronucleus during the process of egg fertilization. While a fertilized (single cell) ovum may thus be called an embryo, the single cell embryo is also specifically referred to herein as a zygote.

Although in ovo activation can be performed on eggs as old as 2 weeks if the eggs are maintained at room temperature, ideally newly oviposited eggs are used for the best results. In a preferred embodiment, activation occurs between 0 and 96 hours following oviposition. In a more preferred embodiment, the activation occurs between 0 and 72 hours following oviposition. In an even more preferred embodiment, activation occurs between 0 and 48 hours following oviposition. In a highly preferred embodiment, the activation occurs between 0 and 24 hours following oviposition. Thus, it is preferred that the activating event occur as soon as possible following oviposition. However, the precise timing can depend on how the oviposited egg is maintained, e.g., temperature, humidity, etc. For example, activation can improve if the unfertilized oviposited egg is activated before it is allowed to cool.

In the methods of the invention, activation of the avian egg in the shell is accomplished by mechanically disrupting the ovum or delivering a biological sample, e.g., a sample comprising one or more of a sperm, cell or nucleus, into the oviposited egg. Disruption or delivery of the biological sample may be accomplished by any method which will allow the sample to be delivered inside the shell, including, but not limited to, dissolving an area of the shell with, e.g., an acid solution, using electroporation, and creating an opening by penetrating or cracking an area of the shell, for example using a tool such as a needle or a scalpel.

Preferably, the surface of the area of the shell to be penetrated in order to deliver the sample or disrupt the ovum is sanitized before the sample is delivered inside, to prevent contamination of the egg. Any method which is compatible with the delivery method may be used to sanitize the shell, including, but not limited to, the disinfectant IOFEC-20®, and 3% hydrogen peroxide. The surface of the egg at the intended penetration site may be wiped or sprayed with the disinfectant, or the egg may be immersed in a vessel containing the disinfectant of choice.

As is described above, an opening in the shell can be made with a tool such as a knife or a needle. Preferably, the tool will be sterile. For example, in a two-step procedure, an opening in the shell can first be made with a knife or other sharp instrument. In a second step, a needle attached to a syringe containing a sample can be passed through the opening to deliver the sample into the egg. Introduction of the sample into the opening in the shell may also be accomplished by other means, including, but not limited to, the use of a pipette, such as a micropipettor. Alternatively, in one step, a needle attached to a syringe containing the sample can be used to penetrate and thus create the opening in the shell and deliver by injection the sample into the egg. Thus, "opening" can include a hole created by a needle. Of course, one of ordinary skill in the art will be able to choose a needle whose gauge will be large enough to allow the sample to be moved through the needle. In one embodiment, the needle will be of the smallest gauge that can deliver intact into the shell and also be sturdy enough to penetrate the calcium eggshell. Alternatively, a separate needle or other device could be used to make the opening in the eggshell. Typically, needles varying from 30-gauge to 16-gauge can be used. In one embodiment a 22-gauge needle is used.

The opening can be made anywhere in the shell that effects viable activation, but is typically made in an area of the shell that is near the germinal disc. While an egg may be manipulated so as to place the germinal disc at different regions of the egg, the germinal disc in a newly oviposited egg is typically located at the large end of the shell, which overlies the air cell adjacent to the yolk. Once an opening has been created in the shell, the sample is preferably delivered by introducing the needle, pipette, etc., through the air cell and beneath a membrane lying below the air cell (inner shell membrane).

Preferably, to prevent contamination of the egg and death of an embryo, the opening in the shell is sealed. A non-toxic adhesive can be applied directly to the opening in the shell to seal it. Alternatively, a piece of eggshell can be used as a patch to close the opening and may be attached to the shell with a non-toxic adhesive. In one embodiment, the non-toxic adhesive is Elmer's® glue. In another embodiment, the adhesive is a silicone sealant. Moreover, any "tissue glue" can also be used to seal the shell. A "tissue glue" is a sterile, non-toxic adhesive used during surgical, operative procedures to bind tissues together.

The method of the present invention can be used to activate oviposited eggs from avian species selected from the group consisting of chicken, quail, duck, turkey, pheasant, ostrich, emu, goose, peafowl, grouse, rhea, parrot, cockatiel, cockatoo, parakeets, and other commercially valuable birds.

The present invention also provides a method of activating an avian egg in a shell, wherein the egg comprises a yolk enclosed by a membrane, and hatching a live chick.

After the activation according to the methods of the present invention as described, the egg is incubated until the live chick is hatched. One of ordinary skill will be aware of the amount of time and the preferred conditions for incubating a fertilized egg belonging to a particular species. The following are incubation periods for various species of birds: Chicken—21 days, Quail—23 days, Corunix quail—17 to 18 days, Pheasant—23 days, Turkey—28 days, Duck—28 to 33 days, Goose—28 to 30 days, Parakeet—18 days, Parrots—28 days, Dove—14 days, Mynah—14 days, Finch—14 days, Button Quail—16 days, Valley Quail—21 to 22 days, Swan—30 to 37 days. Incubation of eggs fertilized by the methods of the present invention as compared to naturally fertilized eggs may differ only in that the length of incubation time may be lengthened to include the amount of time that the fertilized egg would have spent within the body of the female prior to oviposition. In a preferred embodiment, the incubation period lasts from 21 to 23 days for chicken eggs. While one of ordinary skill in the art will readily be able to determine the optimal temperature for incubation of an egg from a particular species of bird, typically the incubation temperature is between 95° F. and 100° F. A chicken egg will be incubated at about 99.5° F. In a more preferred embodiment, the temperature at which the chicken egg is incubated will be lowered as the egg nears the point of hatching. Thus, in a currently preferred embodiment, a chicken egg is incubated at 99.5° F. from day 1 of incubation to about day 18 of incubation, and at 98.5° F. from day 19 of incubation to hatching.

As is well known in the art, the humidity level at which an egg is incubated can be important for bringing the egg to hatch. Thus, typically the egg is incubated at between 75% and 90% humidity. Preferably, the egg is incubated at about 80% humidity. More preferably, the humidity level at which the egg is incubated will be raised as the egg nears the point of hatching. Thus, in a preferred embodiment, a chicken egg is incubated at 80% humidity from day 1 of incubation to about day 18 of incubation, and at 85% humidity from day 19 of incubation to hatching. In a specific preferred embodiment, an egg is incubated at 99.5° F. and 80% humidity from day 1 of incubation to about day 18 of incubation, and at 98.5° F. and 85% humidity from day 19 of incubation to hatching. As is well known in the art, turning the eggs during incubation is useful for promoting growth of the embryo.

It is further preferred that the incubation of the eggs take place in a commercial incubator. Commercial hatchers and setters are produced by many companies including PAS Reform, Jamesway, Chickmaster, Buckeye, Cumberland, Petersime, Humidaire Incubator Co., etc. Preferably, the eggs are moved from a setter incubator to a hatcher incubator at about 3 days prior to hatch. The hatcher basket allows the egg to lie on its side where the chick can more easily pip out. This basket also allows the chick to walk about immediately after hatch, which is necessary for the chick's development and viability.

In another embodiment, the present invention provides an oviposited avian egg comprising a native embryo having fewer than 40,000 cells, wherein the embryo can develop into a live chick. "Native" means growing, living or produced in its place of origin. Thus, a native embryo is an embryo that develops and hatches in the same shell in which the female pronucleus was formed. Thus, the embyro is descended from the native ovum. By the time an ovum which has been fertilized naturally has been oviposited, the developing embryo typically has between 40,000 and 70,000 cells. However, the egg of the present invention is fertilized after it has been oviposited in its shell; thus, an embryo developing in the egg of the present invention will at some time during incubation have fewer than 40,000 cells. In fact, at the moment of activation, the embryo in the egg of the present invention will have one cell and is a zygote. As the embryo grows within the egg, normal cell division will occur and the number of cells will increase. Thus, the activated, oviposited egg of the present invention will at some time during incubation comprise an embryo having, for example, 1, 100, 1,000, 10,000, 20,000, 30,000 or 40,000 cells, including between these numbers of cells. Two commercially preferred avian eggs are chicken and turkey.

In another embodiment, the present invention provides an avian egg in a shell comprising an embryo having fewer than 40,000 cells (e.g. 30,000; 20,000; 10,000; 1,000; 100 and 1 (zygote)), wherein the embryo can develop into a live chick, and wherein the shell has an opening of less than 4 centimeters. In another embodiment, the opening in the shell is less than 2 centimeters. In another embodiment, the opening in the shell is less than 1 centimeter or 0.5 centimeter. In one embodiment, the opening in the shell is only large enough to accommodate a 22-gauge needle. Thus, the opening can be any size between the smallest opening that will permit injection of a sample or means to disrupt the ovum, up to smaller than the hole required to place an in vitro fertilized (i.e., outside the shell) ovum back into the shell. By "opening" is meant a hole has been made in the egg at some point after oviposition. "Opening" includes an egg where the hole has subsequently been sealed. For example, an egg having a hole created by a needle used to inject a sample and then sealed is, even after sealing, within the definition of avian egg having an opening. The embryo can be either native or non-native to the egg. "Non-native" includes embryos developed from an ovum not native to the shell in which it was oviposited. Two commercially preferred eggs are chicken and turkey. In addition, the invention provides an oviposited avian egg comprising an embryo and a native yolk wherein the embryo has fewer than 40,000, 30,000, 20,000, 10,000, 5,000, 1,000 or 100 cells, including numbers in between 1 and 40,000. The chicks which hatch from these eggs can have a normal karyotype and normal development.

An egg of the present invention may, for example, be derived from avian species selected from the group consisting of chicken, quail, duck, turkey, pheasant, ostrich, emu, goose, peafowl, grouse, rhea, parrot, cockatiel, cockatoo, parakeets, swan, dove, and other commercially valuable birds. In a commercially preferred embodiment, the egg is derived from avian species used in the methods of the present invention and is selected from the group consisting of chicken, turkey, goose, duck, quail, and pheasant. In a more preferred commercial embodiment, the egg is derived from a chicken. The method can also be effectively utilized on avian species in zoos, e.g., to help preserve endangered species.

The methods of the present invention can also be used for in ovo activation of reptilian eggs. Reptilian eggs, similar to avian eggs, comprise a yolk and female pronucleus and are protected by a shell when they are laid. An unfertilized, oviposited reptilian egg can be activated in the shell according to the methods of the present invention.

The in ovo activation methods described herein can also be utilized in conjunction with other in ovo procedures. For example, the embryo can be vaccinated after activation. Such vaccination procedures are well known to those skilled in the art. Alternatively, such vaccination could occur simultaneously with in ovo activation, provided that the vaccine did not prevent development of the embryo.

Additionally, in ovo activation can be automated such that multiple eggs are simultaneously activated by, for example, injection techniques. Thus, 50, 100, 200, 300 or more eggs could be simultaneously activated.

The unfertilized oviposited egg can be activated by various specific activation methods as set forth below. The activation methods described above can be accomplished for example with fertilization, parthenogenesis, and nuclear transfer. Thus, for example, as described below, the sample delivered for activation of the oviposited unfertilized egg could be a sperm comprising sample.

Fertilization

The present invention provides a method of fertilizing an avian egg in a shell, wherein the egg comprises a yolk enclosed by a membrane, comprising obtaining a sperm sample comprising avian sperm in a physiologically acceptable carrier, and delivering the sperm sample into the egg, so as to fertilize the egg. The process of fertilizing an oviposited egg in a shell is referred to herein as "in ovo fertilization" (IOF).

The sperm in the sperm sample may be obtained from a bird by methods known to a person skilled in the art, such as the abdominal massage method which is well-known to those of skill in the art. This method allows the collection of an ejaculate (semen) comprising sperm, seminal fluid, and transparent fluid. Transparent fluid is a lymphlike fluid that passes from the lymph channels to the surface of the phallus during phallic tumescence. Avian sperm may also be obtained from commercial sources that are well known to those of skill in the art.

In one embodiment, the sperm in the sperm sample is from a single bird. In another embodiment, the sperm in the sperm sample is a mixture of sperm obtained from more than one bird. When a mixture of sperm from more than one bird is used in the methods of the invention, the probability of successfully fertilizing the egg can increase, because if one of the birds from which the sperm has been collected is infertile, it is possible that the sperm collected from the other bird or birds will be capable of fertilizing the egg.

In a preferred embodiment, the sperm sample comprises sperm from birds which are members of the same species, and the sperm sample is used to fertilize eggs oviposited by hens which are members of the same species as the sperm donors. The present invention also contemplates the use of sperm from one species and an egg from another species, if the sperm is capable of fertilizing the egg.

While it is typically preferred that the sperm be used within 30 minutes of the time that it is collected, older sperm, and even sperm which have previously been frozen or freeze dried may be used in the methods of the invention, as long as the sperm retain their ability to fertilize an ovum. Where the sperm are to be used more than 30 minutes after collection, it is preferred that they be combined with a sperm extender, as is described below.

As mentioned above, the sperm sample also comprises a physiologically acceptable carrier. As used herein, a "physiologically acceptable carrier" is a fluid in which sperm remain motile and viable. Examples of a physiologically acceptable carrier include, but are not limited to, unaltered semen, seminal fluid (either original to the sperm or added), transparent fluid (either original to the sperm or added), buffered saline solution, sperm extender, and combinations thereof. Preferably, the carrier includes sperm extender, also referred to in the art as a diluent. As mentioned above, the use of a sperm extender is especially preferred where the collected sperm will not be used for fertilization within 30 minutes after collection. M. R. Bakst, *In Manipulation of the Avian Genome*, R. J. Etches and A. M. Verrinder Gibbons, eds., CRC Press, Boca Raton, Fla., pp. 15-28 (1993). As used herein, a "sperm extender" is a physiologically acceptable carrier that is used to dilute a sperm sample to produce a sperm sample of greater volume in which the sperm are less concentrated. Preferably, the composition of the sperm extender will extend the shelf life of the sperm, as well as diluting the sperm so as to increase the number of eggs which may be fertilized by the quantity of sperm which has been collected. Examples of sperm extender compositions, suggested dilution rates, optimal storage times and conditions, and commercial sources of extender may be found in Bakst ("Preservation of Avian Cells: In: *Poultry breeding and Genetics*, R. D. Crawford (ed.) Elsevier, N.Y., pp 91-108 (1990)). Other diluents commonly used in the poultry industry are Lago Formulation Avian Semen Extender by Hygeia Biological Laboratories, Semaid Turkey Extender by Poultry Health Laboratories in Davis Calif., Beltsville Poultry Semen Extender by Tri Bio Laboratories, Inc. in State College, Pa. In a preferred embodiment, the sperm extender is Avidiluent. Avidiluent is produced by IMB, 10 rue Georges, Clemenceau, BP 81, 61302 l'Aigle, France. Thus, in one embodiment, the sperm sample may comprise sperm and seminal fluid, i.e., semen. Moreover, the sperm sample may comprise sperm and seminal fluid which is diluted with a physiologically acceptable carrier, including but not limited to buffered saline solution and a sperm extender.

The sperm sample can also be prepared by methods which will be clear to one of ordinary skill in the art, such as washing semen from one or more birds with a solution such as buffered saline solution or sperm extender, centrifuging the resulting solution, removing the supernatant, and resuspending the washed sperm in a volume of a solution such as buffered saline or semen extender. One of ordinary skill in the art will readily understand how to achieve the desired concentration of sperm by resuspending the sperm in the appropriate volume of solution. For example, following centrifugation and removal of supernatant, the packed sperm may then be weighed, and the number of sperm then estimated by using known values for the weight of avian sperm. The sperm may then be resuspended in the volume required to obtain the desired sperm concentration. Alternatively, the centrifuged sperm may be resuspended following removal of the supernatant, and then recentrifuged, allowing the determination of the packed sperm volume. (Johnston, 1998). Subsequently, the concentration of the sperm may be calculated using the formula of Maeza and Buss. (Poultry Sci. 55:2059 (1976)).

Typically, the concentration of sperm in chicken semen is from 300 million to 800 million per milliliter, in turkey semen from 800 million to 1.5 billion per milliliter, in Guinea fowl semen from 400 million to 800 million per milliliter, in Pekin duck semen from 20 million to 600 million per milliliter. The standard number of sperm used for artificial insemination is 100 million in a total volume of 50 microliters. In the methods of the present invention, because sperm are placed directly adjacent to the female pronucleus, far fewer sperm are required to fertilize the egg. Thus, as few as one sperm can be used in the methods of the present invention. In fact, a large range of sperm concentrations can be used in the present invention. In one embodiment, chicken semen is diluted with an equal volume of Avidiluent and approximately 0.01 milliliters of this sperm sample is injected into an egg. Thus, approximately 1 million sperm would be deposited adjacent to the female pronucleus.

In one method of the invention, fertilization of the avian egg in the shell is accomplished by delivering the sperm sample into the egg. Delivery of the sperm sample may be accomplished as described above. A sperm is approximately 0.5 um at its widest point and 100 um in length. Therefore, in a preferred embodiment, a needle with an inner diameter of at least 10 um can be used for injections. In one embodiment the needle can remain in the shell after injection. Various needles and methods now used for injection of vaccines into eggs could be used or adapted for delivery of sperm.

The opening can be made anywhere in the shell that effects viable fertilization, but is typically made in an area of the shell that is near the germinal disc. While an egg may be manipulated so as to place the germinal disc at different regions of the egg, the germinal disc in a newly oviposited egg is typically located at the large end of the shell, which overlies the air cell adjacent to the yolk. Once an opening has been created in the shell, the sperm sample is preferably delivered by introducing the needle, pipette, etc., through the air cell and beneath a membrane lying below the air cell (inner shell membrane). The sperm number can be increased or decreased, depending on where and in what form the sperm are administered. In a further preferred embodiment, the sperm sample is delivered into the egg using a needle. In nature, the sperm cells must penetrate the inner perivitelline membrane and fuse with the oolema for successful fertilization to occur. With IOF, the sperm cells must also penetrate the outer perivitelline membrane before successful fertilization can occur. To increase the fertilization efficiency, one can treat the OPL or yolk membrane. Any treatment which rendered the OPL or yolk membrane more permeable to sperm could be utilized, for example, a non-toxic acid, a proteolytic enzyme or physical abrasion.

In one embodiment, the needle, pipette, etc., is advanced through the shell at an angle of approximately 15°, penetrating the membrane lining the shell. In a method of the invention, the needle, pipette, etc., can be advanced through the air cell, until it meets the inner shell membrane. A person practicing the method of the invention will know that the tip of the needle, pipette, etc., has encountered the membrane when slight resistance to further advancement of the tip is felt. As the tip is gently advanced, the resistance from the membrane gives way and the tip is allowed to barely penetrate the membrane. The sperm sample can then be delivered into the egg, adjacent to a region of the membrane and that is adjacent to the germinal disc. Therefore, the sperm can be delivered just under the membrane, a procedure called intracytoplasmic sperm injection (ICSI). Typical volumes of the sperm sample are as small as 0.005 ml or as large as 0.10 ml. A typical volume of injected sperm sample is about 0.01 ml.

Preferably, to prevent contamination of the egg and death of an embryo, the opening in the shell is sealed as described above. As described above, the method of the present invention can be used to fertilize oviposited eggs from avian species selected from the group consisting of chicken, quail, duck, turkey, pheasant, ostrich, emu, goose, peafowl, grouse, rhea, parrot, cockatiel, cockatoo, parakeets, and other commercially valuable birds.

The present invention also provides a method of fertilizing an avian egg in a shell, wherein the egg comprises a yolk enclosed by a membrane, and hatching a live chick, comprising obtaining a sperm sample comprising avian sperm in a physiologically acceptable carrier, delivering the sperm sample into the egg, so as to fertilize the egg, incubating the egg, and hatching the live chick from the egg. As used herein, "obtaining" includes utilizing pre-made and pre-delivered sperm samples.

After the sperm sample has been delivered into the egg according to the methods of the present invention as described above, the egg is incubated until the live chick is hatched as described above.

As described above, the methods of the present invention can also be used for in ovo fertilization of reptilian eggs. Reptilian eggs, similar to avian eggs, comprise a yolk and female pronucleus and are protected by a shell when they are laid. An unfertilized, oviposited reptilian egg can be fertilized in the shell according to the methods of the present invention. In particular, a sperm sample, comprising sperm from one or more reptiles of the same species, is delivered into the unfertilized, oviposited egg through an opening created in the shell and onto the yolk adjacent to the female pronucleus where fertilization occurs.

As described above, the in ovo fertilization methods described herein can also be utilized in conjunction with other in ovo procedures. For example, the embryo can be vaccinated after fertilization. Such vaccination procedures are well known to those skilled in the art. Alternatively, such vaccination could occur simultaneously with in ovo fertilization, provided that the vaccine did not prevent development of the embryo.

Additionally, in ovo fertilization can be automated such that multiple eggs are simultaneously fertilized by, for example, injection techniques. Thus, 50, 100, 200, 300 or more eggs could be simultaneously injected.

Parthenogenesis

In one embodiment of the present invention, activation of the oviposited unfertilized egg is induced by parthenogenesis. As used herein, "parthenogenesis" is the production of embryonic cells from a female gamete in the absence of any contribution from a male gamete.

In a preferred embodiment, activation by parthenogenesis of an unfertilized oviposited avian egg can be induced by penetration of the membrane that surrounds the yolk (yolk membrane) and germinal disc, for example, by directing a 25-gauge needle through the shell and into the egg to penetrate the membrane surrounding the yolk. Preferably rupture of the yolk is avoided. Thus, penetration and disruption of the membrane surrounding the yolk can initiate activation of the ovum. It is contemplated that other mechanical means of disrupting the membrane surrounding the yolk can be used. For example, lasers, including a non-thermal YAG (yttrium-aluminum-garnet) laser, can be used to disrupt the membrane surrounding the yolk, instead of using a needle in this procedure.

There is evidence that it is the transient increase in cytosolic $Ca^{2+}$ that initiates the program of egg development. The cytosolic concentration of $Ca^{2+}$ can be artificially increased either by injecting $Ca^{2+}$ directly into the egg or by the use of $Ca^{2+}$ carrying ionophores such as A23187. This activates the eggs of all animals tested so far (Alberts 1983). Preventing the increase in $Ca^{2+}$ by injecting the $Ca^{2+}$ chelator EGTA inhibits egg activation after fertilization. Because the increase in $Ca^{2+}$ concentration in the cytosol is transient, lasting only for 2 to 3 minutes after fertilization, it is clear that it cannot directly mediate the events observed during the later stages of egg activation including DNA and protein synthesis. Instead, the rise in $Ca^{2+}$ concentration serves only to trigger the entire sequence of developmental events; some more permanent change must take place in the egg while the $Ca^{2+}$ level is high.

While the mechanism of activation is not fully understood, it is clear that the sperm serves only to trigger a preset program in the egg. The sperm itself is not required. An egg can be activated by a variety of nonspecific chemical or physical treatments. These processes are also generally thought to raise intracellular $Ca^{2+}$ (Rickord and White, 1992). For example, pricking with a needle can activate a frog egg. (Alberts, 1983). Mouse oocytes have been activated by exposure to $Ca^{2+}$ —$Mg^{2+}$ free medium (Surani and Kaufman, 1977), medium containing hyaluronidase (Graham, 1970), exposure to ethanol (Cuthbertson, 1983), $Ca^{2+}$ ionophores or chelators (Steinhardt et al., 1974; Kline and Kline, 1992), inhibitors of protein synthesis (Siracusa et al., 1978) and electrical stimulation (Tarkowski et al., 1970). Activation of bovine oocytes has been reported by ethanol (Nagai, 1987), electrical stimulation (Ware et al., 1989), exposure to room temperature (Stice and Keefer, 1992), and a combination of electrical stimulation and cycloheximide (First et al., 1992; Yang et al., 1992). These methods can be applied to unfertilized oviposited avian eggs.

One application of in ovo activation by parthenogenesis is the rapid production of pure inbred lines of breeding stock. Current industry practice involves the use of different combinations of homozygous parent lines to produce unique commercial bird products. Much effort is put into obtaining, improving and maintaining these pedigreed lines. With parthenogenesis, a female gamete can be induced to develop into a live chick without a genetic contribution from the male. The resulting chick is entirely homozygous at every allele. Thus, homozygous pedigreed lines can be created in one generation instead of the multiple rounds of inbreeding required today. Furthermore, instead of using populations of birds to derive the homozygous line, a single superior individual can be used. Because there are individual birds in a breeding population that greatly outperform the average, this method is a way to rapidly get the best available genetic traits into the final commercial product.

Nuclear Transfer

Nuclear transfer/cellular micromanipulation technologies can be utilized to activate an unfertilized oviposited avian egg. Thus, a separate contemplated embodiment of the present invention involves the delivery of fluid suspensions containing cellular nuclei or "nucleoplasts." Nucleoplasts can be generated on a large scale using certain advanced centrifugation procedures. In many species, such as sheep, cow and mice, it has been determined that a nucleoplast isolated from one cell can be inserted into another enucleated cell for the purpose of generating an identical, cloned individual. As used herein, "nuclear transfer" is the insertion of a nucleus, also known as a nucleoplast, (either in a cell or as a nucleus independent from a cell), into another cell in which the native nucleus is ineffective, e.g., by removal or ablation. The procedures described herein allow producers to efficiently propagate elite genetic pedigrees into commercial flocks and serve as the basis for development of an automated nuclear transfer instrument platform.

The primary steps required for the implementation of this strategy are as follows: (1) development of suitable cell lines and conditions for the cultivation of nucleoplast donors; (2) visualization and removal or ablation of nuclear structures within avian ova and/or zygotes; (3) isolation of donor nuclei (4) transfer of donor nuclei into ova (cytoplasts). Activation of reconstituted ova leading to embryonic development may also be effected.

Nucleoplast Donor Cells. Embryonic stem cells and primordial germ cells have been shown to remain totipotent in the chicken and can be utilized in an avian NT procedure. Cloned chickens generated in this fashion can be valuable for applications in certain poultry breeding schemes.

Alternatively, somatic cell lines can be advantageous for other poultry breeding scenarios. A factor in the selection of a somatic cell type is its ability to undergo "reprogramming." Reprogramming can be utilized in order for the nucleoplast to contribute to all embryonic cell lines and thus lead to normal embryonic development. Cultured Embryonic Fibroblasts (CEF) have been widely utilized in mammals with good results due to their ease of culture and genetic manipulations. CEFs can be used for somatic cell nuclear transfer in the avian system. Alternatively, embryo-derived blastodermal cells (BCs) have been cultured and can be used. Yet another cell type that can be used with the avian nuclear transfer platform is an avian B cell.

An advantage of using avian B cells is their ability to undergo high levels of recombination. This ability can be important because it makes the process of getting exogenous DNA incorporated into the avian genome much more efficient. Modifications performed in any of these donor cell lines in vitro are then incorporated into the genome of the resulting bird. Tests can be performed to identify the most advantageous cell type. For example, nucleoplasts can be created from these cell types and transferred to the avian cytoplast (recipient cell). Those cell types leading to the highest rate of embryonic survival can be incorporated into the standard technology platform.

Nuclear transfer in mammals has been successfully carried out using both ova and zygotes, although ova are predominantly used for this purpose. Standard nuclear transfer procedures typically require the removal of or ablation of the existing cellular nucleus, preferably before the introduction of the donor nucleus. Avian eggs are large and the distance between a donor nucleus and the nucleus of a recipient cell is great enough that removal of the nucleus of the recipient cell is not strictly required. However, it is presently preferred that enucleation occur.

The cell nucleus in an avian egg is obscured by dense yolk granules making traditional light microscopy largely ineffective for visualization. For this reason the current method of choice for enucleating avian ova involves the use of fluorescent nuclear labeling. Known fluorescent nuclear dyes such as Hoescht 33342 (bis-benzarnide) and DAPI (4'6'-diamidino-2-phenylindole, hydrochloride) can be utilized for their ability to effect maximum visualization of the nucleus and its associated DNA.

Two standard strategies can be utilized for enucleation; (1) removal via glass micropippette or (2) ablation with lasers. Both strategies for cellular micromanipulation are currently in use. Laser type and wavelength can be determined empirically. Elimination of the fluorescent area within the cytoplasm by either method would indicate removal of the nucleus. It is preferred at this phase to remove not only the nuclear DNA but also the spindle forming machinery.

A number of factors influence development after nuclear transfer including a requirement that the reconstructed embryo maintain normal ploidy. When a nucleus is transferred from a cell that has begun to differentiate, the pattern of gene expression can be "reprogrammed" from that of a differentiated cell type to that of an early embryo. Experiments in which cell cycle has been varied also suggest that the efficiency of this process is influenced by both the donor and recipient cell cycle stage.

From mammals it appears that the cell cycle stage of both donor and recipient cells influence when DNA replication occurs in the reconstructed embryo. Due to the influence of meiosis promoting factor (MPF) in the cytoplasm, the recipient cell may have a greater influence (Barnes et al., 1993; Campbell et al., 1993). MPF activity during replication can increase at the time of formation of the spindles and can remain high during metaphase II. Nuclear transfer to a cytoplast with a high level of MPF can be followed by nuclear membrane breakdown, chromosome condensation, reformation of the nuclear membrane and DNA replication regardless of the cell cycle stage of the donor nucleus. In contrast, the nucleus determines whether DNA replication occurs following transfer to an oocyte with a low level of MPF activity (Campbell et al., 1993, 1994). From this work it is believed that there are two effects: (1) a greater opportunity for reprogramming of gene expression during specific phases of the cell cycle; and (2) a benefit from transfer to similar phases of the cell cycle.

It has been shown that embryonic development can be enhanced when donor nuclei are in the G0 or G1 phase of the cell cycle. Dolly the sheep developed from an enucleated oocyte fused with a mammary-derived cell presumed to be in G0. Likewise, Cumulus cells in the G0 and G1 states have been used to achieve somatic cell nuclear transfer in mice (Wakayama, et al, 1998). However, cloned calves have been produced using nuclei from non-quiescent donor cells (Cibelli et al, 1998). This indicates that the requirements for successful nuclear transfer in poultry will have to be determined empirically. Cells in various cell cycle stages can be utilized to determine the optimum protocol. Delivery of donor nuclei has been performed both via electrofusion of donor cells to enucleated ova/zygotes and via direct injection of donor nuclei into enucleated ova. Given the large size of avian eggs and the ease of performing injections, direct injection of donor nuclei can be the optimal method of delivery. When nuclear transfer is performed into metaphase II arrested ova, typically it is required to artificially activate the ova. This can be performed at various time intervals ranging from simultaneous with, to several hours after nuclear transfer. These same parameters can be tested for the optimum time of activation.

An automated high-throughput system can be designed to carry out the process. This has the potential to eliminate an entire layer of the poultry industry called "multiplication breeding." Typically in multiplication breeding several generations are needed to go from pedigreed lines through grandparent lines, parent lines and finally to the commercial birds. Populations of birds are required for this process to work. IOA with nuclear transfer can produce the final commercial product from a single superior bird. The net effect is to produce flocks of genetically superior birds in an extremely efficient breeding operation. Furthermore, the cells utilized for nuclear or cellular transfer can be stored indefinitely until a particular commercial product is requested by the end-user. An equally important benefit would be the ability to produce entire flocks of unisex birds. For instance, broiler producers could request all male flocks for increased growth efficiency while egg producers would obviously prefer all female flocks.

Transgenesis

The present invention also provides a method for producing an avian embryo containing heterologous nucleic acid comprising, activating, e.g., fertilizing, an avian egg by the methods of the present invention disclosed herein, and introducing a heterologous nucleic acid into the avian egg. As used herein, nucleic acids include, but are not limited to, DNA, cDNA, RNA, mRNA and antisense RNA. The nucleic acids may be single, double, or multiple-stranded. Heterologous nucleic acids can include nucleic acids not native to the avian species and nucleic acids not normally expressed in the introduced location in the cell or nucleus of the avian species.

After an avian egg has been activated by IOA, the developing embryo can be accessed at any stage of development to manipulate the genetic makeup of some or all of its cells. Of greatest interest for creating transgenic birds is the early embryo. IOA allows for germ line transmission of the heterologous nucleic acid as it allows the earliest possible introduction of heterologous nucleic acid into the early avian embryo. This genetic manipulation of the developing embryo can, for example, produce transgenic birds comprising genetic material which can be used to modulate endogenous DNA and its expression and to create cells which can manufacture commercially valuable proteins for commercial use.

Transfer of a nucleic acid into the avian genome can be performed by a person skilled in the art according to several known methods. (Harlow and Lane, Antibodies: A Laboratory Manual, Cold Spring Harbor Laboratory, Cold Spring Harbor, N.Y., 1988; Lennette et al., Manual of Clinical Microbiology, 14th Ed., Amer. Soc. for Microbiology, Washington, D.C., 1985; Sambrook et al., Molecular Cloning: A Laboratory Manual, 2nd Ed., Cold Spring Harbor Laboratory, Cold Spring Harbor, N.Y., 1989; Antisense RNA and DNA, D. A. Melton, Ed., Cold Spring Harbor Laboratory, Cold Spring Harbor, N.Y. (1988))Freshney, Culture of Animal Cells, A Manual of Basic Technique, 2nd Ed. Alan R. Liss, Inc., New York (1987); Centers for Disease Control Laboratory Manual, U.S. Department of Health, Education, and Welfare Pub. No. 79-8375, p. 75, Centers for Disease Control, Atlanta, Ga.; Fundamental Virology, 2nd Ed. Bernard N. Fields and David M. Knipe, Chief Eds., Raven Press: New York, 1990). Examples of methods of transferring genetic material into the avian genome include, but are not limited to, avian leukosis virus (ALV) transduction mediated transgenesis, transposon mediated transgenesis, blastodermal cell mediated transgenesis, primordial germ cell mediated transgenesis and nuclear transfer. The heterologous nucleic acid may be introduced into the embryo at the same time that the activating event occurs, e.g., at the same time the sperm sample is introduced into the egg, or at a later stage of embryonic development.

A standard method now in use for producing transgenic birds is to produce replication deficient ALV-derived transducing particles comprising a heterologous DNA insert. Because the particles are not capable of replicating in the bird, there is no risk of causing viremia and illness in the bird or humans. The transducing particles can be administered directly to the oviposited egg comprising the early avian embryo using the methods described herein. For example, a window can be generated just above the embryo and transducing particles introduced into the subgerminal cavity of the embryo. The window is then sealed, and the eggs are placed into incubators for development.

Another method used to transfer heterologous nucleic acid into the avian genome is transposon-mediated transgenesis. Transposons are genetic elements that are able to translocate or move about within the genome of their host species. There are no known transposons that occur in avian species. However, it has been shown that certain transposons, reconstructed from other sources, are able to function within the avian genome. These transposons can be engineered to serve as useful nucleic acid vector systems for inserting genes into the avian genome.

Further, another method for introducing heterologous DNA into an avian embryo is blastodermal cell transgenesis. Blastodermal or other early cells can be taken from stage X embryos (the embryonic stage at which a fertilized egg is laid) can be injected back into recipient embryos where they colonize and grow, giving rise to chimeric chickens. A "chimeric" chicken is composed of cells from two different genetic lineages. Blastodermal cells injected into irradiated host embryos soon after they are isolated have the ability to contribute to all tissues of the resulting bird including the germline (cells that give rise to sperm and eggs and thus to all following generations). Blastodermal cells have been cultured and transfected with DNA by various methods known to persons skilled in the art in an attempt to generate transgenic poultry.

Thus, blastodermal cells or embryonic stem (ES) cells can be injected into an in ovo fertilized embryo to create chimeric poultry. These chimeric poultry can then be crossed and, assuming they have germ line transmission of the blastodermal or ES cells, one can create a clone of the original injected cell.

Moreover, primordial germ cell mediated transgenesis may be used to create transgenic birds. As the developing embryo grows, certain cells are committed to the germline to give rise to the sperm and eggs. These primordial germ cells (PGCs) migrate to the genital ridge of the developing gonad where they lie dormant until the bird reaches sexual maturity. One approach to avian transgenesis is to isolate these PGCs, genetically manipulate them and place them back into a developing embryo for continued development. This technical approach is comparable to the blastodermal cell approach in both the extent to which it is developed and its potential applications. Primordial germ cells have been shown to contribute to the germline when injected into recipient embryos just as blastodermal cells have.

Still another aspect of the present invention involves delivering liquid formulations to the avian egg that provide vital information about the genotypic status or constitution of the individual bird. For instance, DNA and/or RNA probes could be delivered into the avian egg for the purpose of sorting embryos by sex or any other genotype. These probes bind specifically to their target sequences and provide specific information about the genetic makeup of the bird. Labeling the probes with various fluorescent, radioactive, or chemiluminescent molecules provides highly-reliable technology for determining genotypic status. Alternatively, antibodies or other proteins may be utilized in a similar fashion as reporter molecules.

Use of the present invention incorporates nucleic acids into single-celled oocytes and early embryos allows for the incorporation of exogenous DNA into all or most of the cells of the resulting bird. However, in an alternative embodiment, the present invention may be adapted to deliver these nucleic acids and nucleic acid vectors to later stage embryos. One current protocol for the production of transgenic poultry involves the injection of viral particles into the sub-germinal cavity of developing avian embryos. Another application would be for the transient expression of a particular gene product in the avian embryo. Nucleic acid formulations could be delivered with the specific intent of generating egg and/or animal based bioreactor systems. Proteins, antigens and antibodies could also be delivered to the embryo in order to affect gene expression.

The in ovo activation methods described herein can also be utilized in conjunction with other in ovo procedures. For example, the embryo can be vaccinated after fertilization. Alternatively, such vaccination could occur simultaneous with in ovo fertilization providing however that the vaccine did not prevent development of the embryo.

Automation

IOA can be automated such that multiple eggs are simultaneously fertilized by, for example, injection techniques. Thus, 50, 100, 200, 300 or more eggs can be injected simultaneously. It will be clear to those of ordinary skill in the art that the methods of the present invention may easily be applied to a large-scale industrial operation, using automation to activate newly laid eggs. Accordingly, an apparatus which has previously been used, for example, to immunize laid fertilized eggs can be adapted to instead introduce a sperm sample, nucleus, or adapted for parthenogenesis in order to automate the IOA process.

As one skilled in the art appreciates, automated egg handling technologies have been developed simultaneously by many independent inventors worldwide. The technologies existing today involve high-throughput systems for injecting liquid substances into avian embryonated eggs. Examples include the injection of vaccines to improve the immune state of resulting chicks, injection of viruses for the production of human and animal vaccines, and injection of proteins to influence chick health, growth, and the like. Another useful automated system for poultry production allows detection of live versus dead chick embryos based on either candling with various light sources or temperature differentials between neighboring eggs in an egg flat. These technologies, taken together, represent the current state of development in this field. However, there exists a need for a more advanced platform adapted specifically to the needs of avian breeders, a need that the present invention addresses and satisfies.

Recent progress in the area of sperm preservation, taken together with the advent of IOF technology, have made it possible to move towards a much more efficient management model for poultry breeding operations. Several of the important genetic technologies described below can be linked together to create a truly versatile platform for the automation of poultry breeding technologies.

In order to perform IOA, e.g., IOF, in an automated fashion, two steps are contemplated. The first step involves calculating the number of sperm cells in the sperm sample, or sample containing cells or nucleus containing material for transfer, that is loaded onto the machine. This task can be accomplished through the use of an integrated spectrophotometer unit (sometimes called a densimeter) similar to those marketed by Animal Reproduction Systems of Chino Calif. and others. This task can also be performed by a flow cytometer. The information obtained from this analysis is communicated to a central processing unit or other analyzing system, in which optimal volumes of sperm and semen extender (diluent), or cells or nuclear material, are determined. This information is then communicated to a fluid dispensing mechanism, resulting in the correct fluid volumes to be dispensed into a central fluid reservoir of an egg injection mechanism or similar system.

For the second step, the central processing unit activates the egg injection mechanism, which delivers the proper amount of the diluted sperm sample or cells or nucleus containing material formulation into the unfertilized egg to the specific depth and at the appropriate angle to accomplish IOA, e.g., IOF. The process of injection includes perforation of the egg shell by a tubular punch and insertion of an injection needle through the shell membrane and possibly the yolk membrane for delivery of the sample formulation.

The egg injection mechanism may be of a design similar to those manufactured and sold by Embrex, Inc., Merck Inc., and others in the industry. As an example, one design is disclosed in U.S. Pat. No. 4,903,635, entitled "High Speed Automation Injection System for Avian Embryos," which is incorporated herein by reference. As described in the patent, the disclosed device is a high-speed automated injection system for avian embryos, which can inject eggs with fluid substances, specifically an inoculating fluid. The machine includes suction devices which lift eggs out of engagement with surfaces, rather than pushing them, before injecting them. Thus, the machine provides separate mechanisms and devices for first forming an opening in the egg shell and then injecting the avian embryo or the surrounding environment with a fluid substance, avoiding use of a single needle or punch to both puncture the shell of an egg and deliver fluid substances to the interior of the egg. As is also known in the art, the present invention here also contemplates using a single needle both to puncture the shell and to deliver fluid substances. Other relevant patents that disclose injection of fluids into eggs include U.S. Pat. No. 5,900,929, entitled "Method and Apparatus for Selectively Injecting Poultry Eggs"; U.S. Pat. No. 5,722,342, entitled "Ovo Antibiotic and Microbial Treatment to Diminish Salmonellae Populations in Avians"; U.S. Pat. No. 5,699,751, entitled "Method and Apparatus for in Ovo Injection"; U.S. Pat. No. 5,438,954, entitled "Method and Apparatus for Early Embryonic in Ovo Injection"; U.S. Pat. No. 5,339,766, "Method of Introducing Material into Eggs During Early Embryonic Development"; U.S. Pat. No. 5,176,101, "Modular Injection System for Avian Embryos"; U.S. Pat. No. 5,158,038, "Egg Injection Method, Apparatus and Carrier Solution for Improving Hatchability and Disease"; and U.S. Pat. No. 5,136,979, "Modular injection system for avian embryos," all of which are incorporated by reference. In the simplest embodiment for IOF, sperm is substituted for antigen in these machines and the depth of injection is adjusted to accomplish IOF.

The process of IOA, e.g., IOF, makes it possible to design systems capable of high-throughput operation for the activation, e.g., fertilization, of avian eggs after they reach the hatchery. Advantageously, the present invention for IOF requires much smaller quantities of sperm for this direct fertilization approach, making it possible to streamline operations by reducing dramatically the number of males in the breeding scheme. The remaining males could be centrally housed with enough fresh sperm being delivered directly to the hatchery to fertilize the billions of eggs hatched in the industry every year. The use of fewer males would allow breeders to make more rapid genetic progress in improving their lines by using only the very elite performers for inseminations. In addition, the industry's infrastructure could be re-rationalized based on the elimination or significant reduction of males. For instance, a much more efficient commercial egg laying operation could be directly substituted for the existing hatching egg facilities since only unfertilized eggs are required. In artificial insemination programs where females represent from approximately ninety-five to ninety-eight percent (95-98%) of the flock, it will be possible to eliminate the need for manual insemination, and thus remove approximately over ninety-five percent (95%) of the current labor requirement associated with these programs.

For automated activation by nuclear transfer, one can further adapt the egg injection mechanism to include a means to render the native nucleus ineffective. For example, the mechanism can include a micropipette or laser to either remove or render the native nucleus ineffective.

In addition to activation, e.g., via fertilization, it is contemplated that the present invention also includes the processes of genetic analysis, manipulation, and propagation. As one skilled in the art appreciates, these tools are currently designed for laboratory usage requiring highly-skilled technicians and, accordingly, have been impractical to date for routine usage in the low-margin poultry industry. As implemented in the present invention, many of these technologies are amenable to incorporation into a totally automated platform for use by production personnel, as well as geneticists and other researchers.

The present invention can be designed to include additional mechanisms and steps to deliver various liquid formulations intended to (a) impact gene expression in the avian embryo concurrently with and/or subsequent to In Ovo Activation, e.g., IOF, and/or (b) to provide vital information as to the genotypic status of the embryo. The delivery apparatus may be similar to the egg injection mechanisms for sperm delivery discussed above. The present invention may employ a common fluid reservoir with the sperm or a separate reservoir independent of the sperm, in which separate needles are inserted into the egg for each fluid, or the fluids are injected sequentially through a single needle inserted into the egg.

The present invention is also contemplated to incorporate a detection mechanism to aid in various types of genetic and protein based analyses. One embodiment of this mechanism would involve the use of a light source of the appropriate wavelength, such as, for example, a laser, and a corresponding dye set differentially expressed in the avian egg as an indicator of certain genotypic or physiologic states. For instance, this embodiment could sort eggs by sex utilizing fluoresence-labeled sexing probes, sex-linked promoters and expression systems, fluorescence-labeled sexing antibodies, and the like.

The detection mechanism may, for example, use a CCD camera or other suitable detector of fluorescent signals to activate a sorting and/or identifying mechanism. In another embodiment, the detection mechanism could utilize a scintillation counter for radioaction and/or chemiluminescence-based detection methods for the same general purposes described above. In yet another embodiment, the system could utilize "gene-chip," genetic microarray and/or genetic macroarray technologies for detection purposes, an example of which is that produced by the company Affymetrix.

As one skilled in the art appreciates, classification of birds according to genotype may be used in production operations. Classification of birds by sex allows the optimization of production capacity. That is, males are desired in the broiler industry, while females are desired as layers. Also, the present invention, providing an enhanced ability for geneticists to perform genetic selections based on the automated high-speed identification and genotyping of eggs, results in more rapid genetic progress towards developing improved poultry lines.

Independent of which type of detection is utilized for genotypic classification, another contemplated design involves classifying each egg as "live" or "dead." Simple light and/or temperature mechanisms are also contemplated for this procedure as incorporated in existing systems by PAS Reform, Breuil, and Embrex. For this aspect of the present invention, U.S. Pat. No. 5,900,929 assigned to Embrex is incorporated herein by reference.

Coupled with the sorting devices described below, the present invention injecting the liquid formulation that provides a predetermined indication and the detection thereof provides a versatile platform for all manner of molecular detection applications.

Still another embodiment of the present invention incorporates a liquid sampling device for obtaining liquid samples from the avian eggs. This design uses a vacuum line in communication with a sampling needle, the tip of which is reciprocated to be surrounded by the liquid portion of a respective avian egg and then removed therefrom. Alternatively, the design may use an electro-osmotic gradient, similar to that utilized in the PE Biosystems 310 genetic analyzer, to draw fluid samples into a sampling capillary.

In order to utilize maximally the above-described detection mechanism(s), it may be necessary at certain times to amplify the signal by various techniques. One embodiment for the amplification of a detection signal could be the incorporation of an integrated thermal cycling unit, such as those produced by PE Biosytems, Hybaid MJ Research and others, for DNA amplification. This device would be important—if not essential—for the use of gene chip, micro-array, and macro-array based genotyping devices discussed above.

To obtain more detailed information about the samples being analyzed, it is also contemplated separating the sample molecules based on size, molecular weight, electric charge or other chemical/physical properties. One embodiment of this separations mechanism is an electrophoresis unit. For example, an integrated capillary electrophoresis unit such as or similar to the 310 Genetic Analyzer produced by PE Biosystems could be utilized to separate both nucleic acids and proteins. This embodiment of the present invention would, for instance, be useful for high-throughput genotyping of eggs from a primry breeder's pedigreed lines of poultry.

Ultimately, the data obtained from the above embodiments, either singularly or collectively, can be processed by software in a central processing unit or other device to evaluate the value and status of eggs as they come off the processing line. The evaluated eggs can be labeled, sorted, and transferred to hatching baskets or trays accordingly. Labeling can be performed by an ink jet mechanism, similar to that currently found in Hewlett Packard and Epson printers. Sorting and transfer of the eggs can be performed by automated suction cups and movable belts which transport trays of eggs through the instrument body and to the waiting egg carts. Mechanisms for this part of the instrument could use designs similar to systems manufactured and sold by Breuil, Kuhl Corporation, Pas Reform, and Embrex.

The instrument platform being described here would also benefit from certain existing genetic/protein analysis capabilities. By directly incorporating the analysis capabilities into the platform these procedures could be performed at high-speed and at an industrial scale. Examples where these analysis capabilities would be directly applicable to the commercial poultry industry are described.

EXAMPLES

The following Examples are set forth so as to provide those of ordinary skill in the art with a complete disclosure and description of how the methods claimed herein are performed, and is intended to be purely exemplary of the invention and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °F. and pressure is at or near atmospheric.

Example 1

1. Forty-three freshly laid unfertilized Barred Rock chicken eggs were disinfected by wiping the shells with 3% hydrogen peroxide and placed in racks.
2. Sperm was obtained from 4 barred rock roosters on the same morning and collected in Vacutainer® vials less than 1 hour before the fertilization procedure was performed.
3. Sperm was pooled from the 4 roosters and mixed with 1 ml of Avidiluent®.
4. Sperm mixed with Avidiluent® was drawn into a 1 ml syringe through a 1", 22 gauge needle to form a sperm sample.
5. The needle created an opening in the large, blunt end of the eggshell and passed through the opening at a 15° angle to the surface of the shell.
6. The needle was passed through the air cell until the tip just penetrated the membrane enclosing the yolk and germinal disc.
7. One drop, 0.05 ml, of the sperm sample was injected onto the surface of the yolk adjacent to the membrane.
8. The needle attached to the syringe was withdrawn from the egg.
9. The opening created in the shell by the needle was patched with a small piece of shell, and the patch was secured to the shell with an adhesive such as Elmer's glue®.
10. The eggs were placed in commercial grade setters maintained at 99.5° F. and 80% humidity from day 1 to about day 18 of incubation. The eggs were turned according to methods known in the art and used in commercial setters.
11. On day 19, the eggs were transferred to commercial hatchers and maintained at 98.5° F. and 80% humidity until hatching.

Ten days after the fertilization method of the present invention was performed on 43 eggs, routine candling of the eggs was performed to determine which eggs had been successfully fertilized. Thirty-five eggs of the 43 eggs had been fertilized. Of the 35 fertilized eggs, 32 were successfully brought to hatching, and all but one of the chicks were healthy. Thus, 72% of the 43 oviposited eggs treated by the fertilization method of the present invention produced a healthy live chick.

Example 2

Data on "Hy-Line Variety Brown" commercial brown egg laying hens:
1. 270 freshly laid eggs were collected at 6:30 in the morning.
2. Semen was immediately collected from Black Giant males into diluent at a 50:50 ratio.
3. Eggs and semen were delivered to the lab within 20 minutes of semen collection.
4. Eggs were divided into two groups, experimental and negative control with 135 eggs each.
5. Experimental eggs were injected as previously described with 10 ul of the diluted semen preparation.
6. Negative controls were not injected.
7. Injected eggs were sealed with silicone sealer and placed in the incubator as previously described.
8. Fertility was checked after 5 days and recorded.
9. 33 of 135 eggs (24%) were determined to be fertile in the experimental group. None of the negative control eggs showed signs of development.

Example 3

Parthenogenesis 1. 270 freshly laid eggs were collected in the morning.
2. Eggs were divided into experimental and negative control groups of 135 each.
3. An opening 2-3 mm was created through the eggshell and shell membranes such that the yolk is visible.
4. The membrane that surrounds the yolk and germinal disc was gently "pricked" and/or penetrated, taking care not to rupture the yolk. (Alternatively, creation of the opening and penetration of the yolk membrane can be performed at the same time by simply inserting a 25 gauge syringe needle through the shell and into the yolk).
5. Eggs thus treated were then sealed with silicon sealer and placed in the incubator.
6. Eggs were checked for development at 5 days and development rates recorded before returning to the incubator.
7. Eggs were allowed to develop until hatching when hatch rates and health conditions are recorded.

Results

1. Eggs with ruptured yolks were discarded, leaving 131 experimental eggs and 135 negative controls.
2. Development was checked after 5 days with 7 of 131 (5%) pricked eggs showing obvious signs of embryonic development.
3. Of the 7 eggs showing embryonic development, 5 hatched producing normal healthy chicks.
4. None of the negative control groups showed signs of embryonic development.

Throughout this application, various publications are referenced. The disclosures of these publications, and the references cited therein, in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and example be considered as exemplary only, with a true scope and spirit of the invention being indicated by the claims.

What is claimed is:

1. A system for fertilizing an oviposited unfertilized avian egg in a shell comprising:
   a means for receiving an avian sperm sample;
   a means for calculating the number of sperm cells in the sperm sample operably connected to a means for determining an amount of diluent to add to the sperm sample operably connected to a means for dispensing diluent into the sperm sample; and a means for injecting a diluted sperm sample into an oviposited unfertilized avian egg in a shell.

2. The system of claim 1, wherein the means for calculating the number of sperm cells in the sperm sample is an integrated spectrophotometer.

3. The system of claim 1, wherein the means for calculating the number of sperm cells in the sperm sample is a flow cytometer.

4. The system of claim 1, wherein the means for injecting a diluted sperm sample into an oviposited unfertilized avian egg in a shell comprises a means for perforating the shell.

5. The system of claim 1, wherein the means for injecting a diluted sperm sample into an oviposited unfertilized avian egg in a shell is configured to deliver the diluted sperm sample at a predetermined depth into the oviposited unfertilized avian egg.

6. The system of claim 1, wherein the means for injecting a diluted sperm sample into an oviposited unfertilized avian egg in a shell further comprises:

a means for injecting a heterologous nucleus into the oviposited unfertilized avian egg; and a means for rendering ineffective the nucleus of the oviposited unfertilized avian egg.

7. The system of claim 6, wherein the means for rendering ineffective the nucleus comprises a micropipette.

8. The system of claim 6, wherein the means for rendering ineffective the nucleus comprises a laser.

* * * * *